United States Patent
Pearson et al.

(12) 
(10) Patent No.: US 6,998,109 B1
(45) Date of Patent: Feb. 14, 2006

(54) EMU-BASED FORMULATIONS WITH LIDOCAINE FOR WOUND TREATMENT BY INHIBITING MICROBIAL ACTIVITY

(75) Inventors: Maurine Pearson, Flower Mound, TX (US); Teresa Leigh Barr, Port Townsend, WA (US)

(73) Assignee: Pearson Research & Development Limited, Pilot Point, TX (US)

( * ) Notice: Subject to any disclaimer, the term of this patent is extended or adjusted under 35 U.S.C. 154(b) by 7 days.

(21) Appl. No.: 10/752,820

(22) Filed: Jan. 7, 2004

(51) Int. Cl.
*A01N 25/02* (2006.01)
*A01N 57/00* (2006.01)
*A61K 9/00* (2006.01)
*A61K 31/66* (2006.01)
*A61K 35/12* (2006.01)

(52) U.S. Cl. .................. 424/43; 424/400; 424/520; 424/522; 514/104

(58) Field of Classification Search .............. 424/43, 424/400, 520, 522; 514/104

See application file for complete search history.

(56) References Cited

U.S. PATENT DOCUMENTS

| | | | |
|---|---|---|---|
| 5,698,227 A | 12/1997 | Rivlin | 424/522 |
| 5,849,334 A | 12/1998 | Rivlin | 424/522 |
| 6,444,234 B1 | 9/2002 | Kirby | 424/725 |
| 6,528,040 B1 * | 3/2003 | Pearson et al. | 424/43 |
| 6,579,543 B1 | 6/2003 | McClung | 424/728 |
| 2004/0247707 A1 * | 12/2004 | Le Roy et al. | 424/735 |

* cited by examiner

*Primary Examiner*—Alton Pryor
(74) *Attorney, Agent, or Firm*—Buskop Law Group, P.C.; Wendy Buskop

(57) ABSTRACT

The present formulation is an analgesic, anesthetic and anti-pruritic formulation with from about 10.0 wt % to about 75.0 wt % Emu oil; from about 10.0 wt % to about 33.0 wt % benzyl alcohol; from about 0.25 wt % to about 5.0 wt % allantoin; from about 0.1 wt % to about 5.0 wt % methylparaben; from about 0.1 wt % to about 2.0 wt % propylparaben; and from about 0.5 wt % to about 4.0 wt % of lidocaine, wherein the formulation is adapted to inhibit microbial activity from *Escherichia coli, Salmonella typhimurium, Pseudomonas aeruginosa, Staphylococcus aureus, Enterococcus faecalis, Bacillus cereus, Candida albicans, Streptococcus agalactiae* or combinations thereof, and wherein the lidocaine relieves pain on the epidermis of humans and animals of skin irritations, wounds, or burns.

18 Claims, No Drawings

EMU-BASED FORMULATIONS WITH LIDOCAINE FOR WOUND TREATMENT BY INHIBITING MICROBIAL ACTIVITY

FIELD

Embodiments pertain to Emu oil based formulas that are analgesic, anesthetic and anti-pruritic formulation and also relieve the pain on the epidermis of humans and animals of skin irritations, wounds and burns.

BACKGROUND

Found in the wild only in Australia, Emus (*dromiceius novae-hollandiae*) are the second largest members of the ratite group of flightless birds in the world. The Emu have wings but they are very tiny. They can run up to. 35–40 miles an hour, as they have very large and strong legs. Although a very docile creature, the Emu's legs are so strong; one kick can break a man's leg. Now Emus are being farmed in many parts of the world. They are raised for their valuable products, which include very low fat meat, supple leather hides, decorative and nutritional eggs, and very rich oil, which are obtained from the Emu. Emus are by nature, very healthy and immune to many diseases. Emus are referred to a "living dinosaurs," as their skeletal structure closely resembles some dinosaurs. Emus living today closely resemble their ancestors of millions of years ago.

Emu oil, a food by product, is obtained from the fat of the Emu. It is an all-natural substance. When processed, the fat is taken through a series of steps to refine, sterilize and deodorize the oil. Not all Emu oil on the market is refined. Some Emu oil is simply rendered, which means the oil is simply filtered, and may contain contaminants. Emu oil contains high amounts of EFA's (essential fatty acids). EFA's produce energy in the process of oxidation. In humans EFA's govern growth, vitality and mental state of mind. Oxidation is the central and most important living process in our body.

Emu oil by nature is not regarded as a sterile ingredient. Due to lack of regulatory controls and procedures, Emu oil is processed in many different ways, i.e., some forms of rendering, which is simply a filtration process, which leaves the Emu oil with its natural yellow color, and a slight odor. The present formulation uses a refinement process, which yields a clearly pure Emu oil product, creamy white and odor free. The present formulation utilizes a sterilization technique to render the Emu oil in the present formulation free of contaminants to be used as a preparation and treatment for cutaneous wounds and burn ulcers.

Various patents discuss the use of Emu oil, for example, U.S. Pat. No. 5,662,921 discusses how Emu oil can be use to prevent scarring when applied to a newly received cut or burn. It has been known for a long time that Emu oil also diminishes old scars, even stretch marks. U.S. Pat. No. 5,662,921 discusses how Emu oil increases high-density lipoproteins, preventing and treating scarring. U.S. Pat. No. 5,958,384 teaches that topical or parenteral administration of Emu oil to a mammal stimulates the proliferation of skin, as well as rejuvenating photo-damaged skin. This same patent teaches that Emu oil also stimulates melannogenesis in the skin and it can be used to treat disorders such as hypopigmentation.

Even so, a need has long existed for a formula, using Emu oil which can be used in hospitals, as a sterile formula for treating of wounds, burns, and other dermatological problems, while remaining stable and usable over time without degradation. A need also exists for a formulation that also relieves the pain on the epidermis of skin irritations, wounds and burns.

U.S. Pat. No. 6,071,959 teaches that amide-type local anesthetics have been used medically for many years and is hereby incorporated as reference. They produce a reversible loss of sensation by preventing or diminishing the conduction of sensory nerve impulses near to the site of their administration. They are most often used to ameliorate pain without loss of nervous control. Examples of amide-type local anesthetics are aptocaine, bupivacaine, butanilicaine, carticaine, cinchocaine, clibucaine, ethyl parapiperidinoacetylaminobenzoate, etidocaine, lignocaine (also known as lidocaine), mepivacaine, oxethazaine, prilocaine, pyrrocaine, ropivacaine, tolycaine and vadocaine.

Amide-type local anesthetics may be administered in a wide variety of different ways; some compounds are more suitable than others for a particular route of administration. For example, topical anesthesia works by blocking the sensory nerve endings in the skin or mucous membranes. The amide-type local anesthetics also vary in their anesthetic potency, rate of onset and duration of effect. For example, lignocaine (2-diethylamino-N-[2,6-dimethylphenyl]acetamide) has a fast onset and an intermediate duration of action, and is employed in a wide range of anaesthetic applications.

SUMMARY

The present formulation is an analgesic, anesthetic and anti-pruritic formulation. The formulation is made of about 10.0 wt % to about 75.0 wt % Emu oil; from about 10.0 wt % to about 33.0 wt % bezoin and derivatives thereof; from about 0.01 to about 13 wt % alkyl esters; from about 0.25 wt % to about 5.0 wt % allantoin; from about 0.1 wt % to about 5.0 wt % methylparaben; from about 0.1 wt % to about 2.0 wt % propylparaben.

The formulation can also include from about 0.5 wt % to about 4.0 wt % of lidocaine. The lidocaine relieves pain on the epidermis of humans and animals of skin irritations, wounds, or burns. The formulation is adapted to inhibit microbial activity from *Escherichia coli, Salmonella typhimurium, Pseudomonas aeruginosa, Staphylococcus aureus, Enterococcus faecalis, Bacillus cereus, Candida albicans, Streptococcus agalactiae* or combinations thereof.

The clinical benefits of this formula include reduced wound sepsis rates, improved hempdynamic status, and decreased requirement for donor site harvest. Since engraftment rates are high with good standard care, it is important to evaluate healing outcomes such as durability, functionality, and cosmetic appearance, including scarring. The formula also provides improved quality of healing and products that reduce scarring may also improve function, for example, range of motion, the contour and feel of healed skin, or normalization of skin pigmentation or markings.

The present formulation enables tissue to regenerate, restore, and rebuild in the underlying wound itself and surrounding tissue, therefore fortifying, increasing energy to the existing cells that are not necrotic, and fortifying cells that are necrotic. The formulation is able to improve wound closure time, and facilitation of surgical closures.

DETAILED DESCRIPTION OF THE PREFERRED EMBODIMENTS

The present formulation is an Emu oil based formula that is cable of improved transdermal properties, thus creating healthier cells that proliferate at an accelerated rate. By increasing the feeding of the skin cells, this causes proliferation and thus the theory of Emu oil being biologically active to human skin. The formulation also includes lidocaine to relieve the pain on the epidermis of humans and animals of skin irritations, wounds and burns.

The formulation has a preferred formula of from about 10.0 wt % to about 75.0 wt % Emu oil; from about 10.0 wt % to about 33.0 wt % bezoin and derivatives thereof; from about 0.01 to about 13 wt % alkyl esters; from about 0.25 wt % to about 5.0 wt % allantoin; from about 0.1 wt % to about 5.0 wt % methylparaben; and from about 0.1 wt % to about 2.0 wt % propylparaben.

The formulation can also include from about 0.5 wt % to about 4.0 wt % of lidocaine.

In the preferred embodiment, the formulation is about 61.5 wt % Emu Oil; about 20.0 wt % Benzyl Alcohol; about 2.0 wt % Allantoin; about 1.25 wt % Methylparaben; about 0.40 wt % Propylparaben; and about 2.0 wt % Lidocaine.

The formulation based on Emu oil accelerates wound closure, reduces wound debribement, reduces scar tissue and enhances the smoothness and appearance to the skin while maintaining and feeding skin cells with linoleic acid. The formulation also increases cell proliferation, therefore increasing the ability to heal.

The formulation is adapted to inhibit microbial activity from *Escherichia coli, Salmonella typhimurium, Pseudomonas aeruginosa, Staphylococcus aureus, Enterococcus faecalis, Bacillus cereus, Candida albicans, Streptococcus agalactiae* or combinations thereof. The lidocaine assists in relieving the pain on the epidermis of humans and animals of skin irritations, wounds and burns.

The Emu oil, which is most preferred in this formulation, has a chemical analysis of about 0.33% to 0.02% Free Fatty Acid; about 0.66% Acid Value; a calculated Iodine value between 69.7 and 72.8 mEq/100 g; and an OSI of 11.95 Hours at 110.0 degrees C.

The following table illustrates the fatty acid composition of the Emu oil as compared to human skin.

|  |  | Emu Oil | Human Skin Oil |
| --- | --- | --- | --- |
| Myristic | C:14:0 | 0.3% | 2.1% |
| Palmitic | C:16:0 | 20.3% | 20.2% |
| Palmitoleic | C:16:1 | 3.2% | 3.8% |
| Margaric | C:17:0 | 0.2% |  |
| Margaric oleic | C:17:1 | 0.1% |  |
| Stearic | C:18:0 | 10.1% | 11.2% |
| Oleic | C:18:1 | 51.6% | 30.8% |
| Linoleic | C:18:2 | 13.1% | 15.1% |
| Linolenic | C:18:3 | 0.5% | 0.3% |
| Arachidic | C:20:0 | 0.1% |  |
| Eicosinoac | C:20:1 | 0.5% |  |

Other fatty acids, which may be in Emu oil include elaidic and vaccenic fatty acids.

Analysis of the Emu oil shows calculated iodine content of 72.8%. The present formulation embodies the natural iodine properties of the Emu oil. Iodine has long been known for its antiseptic and germicide properties, in turn helping to accelerate wound closure by minimizing infection. Normally, iodine does not occur naturally in nature. In combination as iodides, it is found in the ashes of certain marine algaes and weeds. Until recently, the most important source of iodine was crude Chile saltpeter, and now is been found in the brine of oil wells. Elementary iodine is toxic. The iodine content in the Emu oil is a naturally occurring property, and no reports of toxicity have been noted.

The present formulation embodies the use of the iodine in the Emu oil as an enhancement to the germicide, fungicide and all around antiseptic properties of the formulation. Topical skin dosages of iodine can be used full strength or diluted to 0.1% for applications to wounds. Typically, the therapeutic index for iodine is among the highest of the antiseptics. Unfortunately, iodine burns are common and largely the result of the use of tinctures and solutions with concentrations higher than tolerated by certain skin types. It is the object of the present formulation to embody the features, values and benefits of the high iodine content of the Emu oil, in its natural state, and in combination with the Emu oil fatty acid composition, creating a buffer against the harmful side effects of typical iodine.

An analysis of fatty acids in Emu oil reveals that the oil contains approximately 70% unsaturated fatty acids. The major fatty acid found in Emu oil is oleic acid, which is monosaturated and which comprises over 40% of the total fatty acid contents. This fatty acid is a known enhancer for penetration and transportation of compounds through the pores of the epidermis, the membrane of the skin, and, thus, delivering the active ingredients into the lipid layer at the cellular level.

Emu oil also contains both of the two EFA's, which are important to human health and include: 20% linoleic and 1–2% linolenic acid. Essential fatty acid are by definition those fatty acids that must be obtained from our diet since the body cannot manufacture them, hence, making them essential as transdermal supplements to nourish and proliferate new skin cells for chronic cutaneous ulcers and burn wounds. As one can see in the analysis of Emu oil to human skin oil, Emu oil so closely resembles human skin oil; it is a natural food for skin cells.

Emu oil is unique, as most land animals have a higher concentration of saturated fats. Typical fat contains both saturated and unsaturated fatty acids. The fats found in land animals have a higher percentage of side chains than do the fats in sea animals. Although unsaturated fats are less efficient storage sites for food energy because they have fewer CH bonds than do saturated fats, they have a distinct advantage for animals that live in cold water. Saturated fats melt at higher temperatures than do unsaturated fats. In cold waters, sea animals with solid fats would have the reduced ability to move. This theory also subject to analysis, and may be proven easier to transport unsaturated fats through the skin structure and membrane into the lipid layer, rather than a saturated fat.

The monosaturated fatty acid, oleic acid, is the major fatty acid in Emu oil. This fatty acid is a known enhancer for penetration and transportation of compounds through the pores, the membrane of the skin, and, thus, delivering the active ingredients into the lipid layer at the cellular level.

Essential fatty acids (EFA's) play two important roles in human physiology. Both derive from their incorporation into the phospholipids of cell membranes. By virtue of their high degree of unsaturation, and, hence low melting points, they decrease membrane viscosity and affect several aspects of membrane function. Nearly all cells contain basic fat and oil substances. Fats are called energy storehouses, as on a weight-by-weight basis; they contain twice as much energy as a carbohydrate or protein. Fats are also a heterogeneous group of compounds, which are characterized by their solubility in solvents such as ether and therefore insoluble in water. Emu oil is rendered primarily from the fat pads of the bird or from what is referred to as the storage lipids. Emu fat is storage fat, as in most animals and organisms, which mean it is the principal form of stored energy. As an energy source, it is completely combustible to carbon dioxide and water. This releases a quantity of energy similar to the combustion of fossil fuel.

The fats, which are not reactive to sodium or potassium are referred to as unsaponofiable fats. The major portion of unsaponificable fraction is the sterols. These are cholesterol and cholesterol like substances, which have a characteristic chemical composition, which may simply be described as closed ring in contrast to the chain or open ring appearance of the triglycerides and fatty acids. The cholesterol molecule is the classic steroid molecule. This molecule is common to a number of chemicals important to humans, for example, the anti inflammatory steroidal hormones such as hydrocortisone, and androgens such as testosterone, the progestogens, the bile acids, the vitamin D, and estrogen. The restoration of hormonal balance has been attributed to the restoration of many normal functions of the body, as well as general health care and maintenance.

Inflammation is the normal response to healing chronic ulcers and burn wounds. Inflammation also causes scar tissue to form. A product that could decrease wound sensitivity and inflammation, but increase moisture content would be desirable. Adequate lubrication aids the healing process by providing moisture in areas where sebaceous glands are depleted or currently dysfunctional, increasing pliability of the wound area, thus improving pigmentation and vascularity.

The present formulation, when topically applied is seen to increase the synthesis of DNA in the epidermis, which is a measure of increase in the proliferative activity of the dermis. It is contemplated that the presence of Oleic acid, a simple triglyceride which contains only one type of fatty acid (oleic acid) enables the present formulation to work effectively. A triglyceride is comprised of a glycerin backbone to which the fatty acids are attached. Naturally occurring triglycerides usually are mixed triglycerides; i.e., they contain more than one fatty acid. An example of a mixed triglyceride is palmmitodiolein, the fatty acid composition of which is, as the name indicates, one molecule of palmitic acid and two molecules of oleic acid. This triglyceride may have structural arrangements other than the one shown, i.e., the fatty acid molecules may be arranged with palmitic acid occupying any of the two possible different positions. Oleic acid is also a monosaturated fat.

In an embodiment of the formulation, the Emu oil is a refined and sterilized Emu oil. The refined and sterilized Emu oil can range from about 60 wt % to about 65 wt % in the formulation. Also, the refined and sterilized Emu oil can include at least 70 wt % linoleic and linolenic acids in combination. The refined and sterilized Emu oil in the formulation can also include 20 wt % linoleic and 1–2 wt % linolenic acid.

Linoleic acid is an essential polyunsaturated fatty acid. Linoleic acid deficiency symptoms include scaly skin and slow to heal wounds. Linoleic acid supplementation may be essential and crucial to fortify slow to heal wounds and strengthen and rebuild the skin by increasing linoleic acid content through the membrane and into the lipid layer, thus allowing and enhancing new skin cell and membrane proliferation, as well as minimizing scar tissue. Linoleic acid is required for the formation and maintenance of the epidermal barrier. The present formulation requires linoleic acid.

The present formulation includes linoleic acid which when transferred to the lipid layer may be crucial to "feeding" the skin cells, creating more energy to burn, thus enhancing skin and membrane cell proliferation and fortification, thus reducing scar tissue as well.

Linoleic acid is required for the formation and maintenance of the epidermal barrier.

Stearic acid is also called octadecanoic acid, one of the most common long chain fatty acids, found in combined form in natural animal and vegetable fats. Commercial stearic acid is a mixture of approximately equal amounts of stearic and palmitic acids and small amounts of oleic acid. In nature stearic acid occurs primarily as a mixed triglyceride, or fat, with other long-chain acids and as an ester of fatty alcohol. It is much more abundant in animal fat than in vegetable fat; lard and tallow often contain up to 30 percent stearic acid. Stearic acid is a natural component of the present formulation.

The composition and structure of the fatty acids of the naturally occurring lipids have an even number of carbon atoms because they are synthesized from acetyl groups, each of which contains two carbon atoms. Fatty acids with 16 (palmitic acid) and 18 (stearic acid) carbon atoms are most commonly found in nature, but the reason for their abundance have not yet been established. Fatty acids constitute important components of lipids in plants, animals and microorganisms. In most cases, they are not found in free form, but instead are bound to other compounds to form fatty acid containing lipid, e.g., neutral lipids (triglycerides) sterols, phosphoglycerides such as lecithin, and sphingolipids such as sphingomyelin.

Two typical fatty acids are oleic and palmitic. Although palmitic acid and stearic acid are the major saturated fatty acids found in animal and plant tissues, significant amounts of other saturated fatty acids such as myristic acid and lauric acid, occur in certain tissues, and lignoceric acid and behenic acid are found in high concentrations in brain sphingolipids. Small amounts of fatty acids with an odd number of carbon atoms are also known, e.g., pentadecanoic acid and heptadeconoic acid.

Emu oil has been used in many preparations over the years for all types of skin complaints and maintenance. It has been noted that Emu oil has a positive effect on chronic cutaneous ulcers and burn wounds. Because a wound represents a breach in the body's natural barrier to microbial invasion, the final formulation of topical products used for the treatment of chronic cutaneous ulcers and burn wounds should be sterile to avoid introducing exogenus microorganisms. With this in mind, a product that could be sterilized for chronic cutaneous ulcers and burn wounds that could contain a high amount of Emu oil would be favorable for the industry. With respect to wounds in general, a spray product would be favorable to avoid touching sensitive areas associated with chronic cutaneous ulcers and burn wounds.

The formulation contemplates that the formula can include sufficient and effective amounts of environmentally safe propellants.

Within the scope of the present formulation, the formulation is used for chronic cutaneous ulcers, which also includes and addresses venous stasis ulcers, diabetic foot ulcer, pressure ulcers, graft sites, donor sites and burn wounds. The present formulation is contemplated as a sterile formulation. The guidance on validation of the manufacture of sterile products can be found in the FDA's submission Documentation for Sterilization Process Validation for Human and Veterinary Drug Products (November 1994), which is hereby incorporated by reference.

The present formulation is usable to reduce debridement on tissue. It is generally accepted that necrotic tissue inhibits wound healing by interfering with tissue repair and promoting microbial growth. Thorough debridement of wounds is therefore considered standard care essential to healing.

The unique formulation can be used in wound pain control.

The addition of liodcaine contributes to the formulation by allowing the formulation to relieve the pain on the epidermis of humans and animals of skin irritations, wounds and burns. Lidocaine, the trade name of Lignocaine, is a powerful local anesthetic administered by injection, or topically to mucous membranes. Lignocaine's chemical formula is C14H22N2OHClH2O. Lignocaine is the most important amide local anesthetic. Lidocaine belongs to the family of medicines called local anesthetics. When Lidocaine is applied to the skin, it produces pain relief by blocking the signals at the nerve endings in the skin. Like other local anesthetics, it slows down the depolarization of the nerve cell membrane. This effect is based on the interaction with a specific receptor site in the sodium channel. Lidocaine reduces the automaticity in the conductive system of the heart by slowing down the diastolic depolarization. Lidocaine can have a stimulating or a sedative effect on the central nervous system.

Lidocaine decreases phase-4 diastolic depolarization and suppresses premature ventricular contractions. In addition, Lidocaine is used to treat ventricular tachycardia and some cases of ventricular fibrillation. Lidocaine also raises the ventricular fibrillation threshold.

Lidocaine is indicated as topical anesthetic for use on normal intact skin of humans and animals for local analgesia, or pain relief. Lidocaine is contraindicated in patients with a known history of sensitivity to local anesthetics of the amide type or any other component of the product.

Lidocaine needles from benzene or alcohol and is insoluble in water. As a local anesthetic, Lidocaine relieves pain, itching, soreness and discomfort due to skin rashes, including eczema and minor burns.

As an alternative embodiment, the formulation can use Lidocaine hydrochloride instead of Lidocaine. Lidocaine hydrochloride which is chemically designated as acetamide, 2-(diethylamino)-N-(2,6-dimethylphenyl)-, monohydrochloride and has the molecular weight of 270.8. Lidocaine hydrochloride is a local anesthetic that is also used intravenously to treat certain cardiac arrhythmias, especially ventricular dysrhythmias.

The present formulation has the active ingredient Lidocaine. Lidocaine is listed in the FDA Federal Register; Volume 48, Number 27, Part 348-External Analgesic Drug Preparations for Over-the-Counter Human Use, pages 5852 to 5869. The FDA Federal Register states that products containing the ingredient Lidocaine or Lidocaine hydrochloride in a range of 0.5 wt % to 4.0 wt % are topical analgesic, anesthetic and anti-pruitic. Topical analgesics depress cutaneous sensory receptors without necessarily abolishing other sensations, such as cause a partial blocking of subcutaneous terminal nerve endings, whereas topical anesthetics completely block pain receptors, resulting in a sensation of numbness.

The present formulation combines two of active ingredients from Section 348.10 of the FDA Federal Register: benzyl alcohol at a range of 10.0 wt % to 33.0 wt % percent and Lidocaine or Lidocaine hydrochloride at a range of 0.5 wt % to 4.0 wt %. Based upon the scope of Section 348.10 of the FDA Federal Register, the formulation contemplates that any of the ingredients from Section 348.10 can be added according to the proposed rules of permitted combinations.

The formulation relates to a spray on product, which is sterilized, a germicide, a bactericide, an antiseptic, an antifungal, and a bacteriastatic agent. If a spray on is used, it can be the preferred embodiment, plus any additional environmentally friendly propellants.

The formula can be modified into the form of a gel, a cream, a lotion, a spray, a patch, or an enhanced oil.

The present formulation additionally inhibits the adverse of affects and allergic reactions to benzoin derivatives.

The present formulation consists of Emu oil as a transdermal facilitator and other components that acts to provide effective transport across the dermis or mucous membranes. This component reduces necrotic tissue, to reduce infection, fight the infection that is in tissue, and keep tissue from growing fungus, or going into sepsis. The Emu oil and components also act as an anti-inflammatory agent.

The present formulation can include analgesic, anesthetic, and anti-puritic ingredients.

The present formulation can additionally contain antimicrobial agents for wound infection control, a topical anti-infective, and elimination of microbial growth and necrotic tissue, which interferes with tissue repair. In addition, the formula can include a topical analgesic/anesthetic at active levels (as set by FDA,) and act as a topical pain control product.

The active ingredients of the product may consist of any of the following, within the established concentration for each ingredient: Emu oil 20–70 wt %, but most preferably 60–65 wt %.

Benzyl alcohol, a bezoin derivative, is listed in a summary of ingredient categories and testing as a category 1 analgesic, anesthetic, and anti-puritic active ingredient. Other examples of bezoin derivatives are NF Benzenemethanol, phenyl carbinol CH2OH, and Benzyl C7H8. The benzyl alcohol, which can be used within the scope of the formulation, involves using esters of benzoic and cinnamic acids in storax, Peruvian balsam, and tolu balsam. A product currently on the market can be used which is made synthetically from benzyl chloride by distilling it from an aqueous solution of potassium carbonate with thorough agitation.

Benzyl Alcohol can be added in weight percents ranging from 10 to 33 percent. The most preferred formulation utilizes 20.0 wt % benzyl alcohol.

The present formulation also relates to use of the formula as a local anesthetic by injection and by application to mucous membranes. Externally the formula can be applied as an ointment or as a lotion in topical preparations and used as a bacteriastatic agent in various parenteral preparations. Externally the formula can also be applied to nasal passages and gum tissues.

The formulation may further include an aromatic alcohol, in amounts from 0.5 to 1.2 wt %, which can be used in a concentration of 0.9% as a bacteriastatic preservative in multiple dose vials of solution or drugs for parenteral therapy. An aromatic alcohol such as Benzyl Alcohol can be used.

Various antimicrobial drugs can be added to the Emu oil, including but not limited to: methylparaban or a benzoic acid, or an alkyl ester such as 4-hydroxy-, methyl ester; or possibly Solbrol made by Charkit Chemical Corporation, P.O. Box 1725, Darien, Conn. 07407; Methyl Parasept made by Charkit Chemical Corporation, P.O. Box 1725, Darien, Conn. 07407; Nipagin or even a Methyl p-hydroxybenzoate (99-76-3) C8H8O3 An antimicrobial additive can be formed by esterifying para-hydroxybenzoic acid with methanol using known techniques. The para-hydroxybenzioc acid is obtained by passing carbon dioxide under pressure into dry potassium phenolate heated to about 200 degrees. The resulting potassium salt is decomposed with HCl yielding the free parabic acid. These components can be added in amounts ranging from 0.25–1.25 wt % and most preferably, 1.25 wt %.

Additional preservatives can be added to the formula such as Imidazolidinyl Urea in concentrations ranging from 0.05 to 1.0%.

Methylparabens and other related esters are para-hydroxybenzoic acids that are odorless and harmless to the skin can be employed in the formula. A combination of two or more esters of para-hydroxybenzoic acid has a "synergistic" antiseptic value, i.e. the antiseptic effect of the combination is greater than the total effect as calculated from the values of the individual components; thus a preparation containing 0.15% of the propyl ester (propylparaben) and 0.05% of the benzyl ester has a stronger antiseptic value than 0.2% of either ester alone. The benzyl ester has a high antiseptic value and is suitable for the preparation of antiseptic creams. The preferred amount of alkyl ester for use in the formulation is between 1 wt % and 13 wt %, most preferably 3.0 wt %.

Parahydroxybenzoic acid esters and mixtures of methylparaben and propylparaben can be used in the formulation with excellent and unexpected results. They are commonly used as antimicrobial preservatives; and the amount of their use is contemplated to be in range of 0.025 wt % and 0.2 wt % of methylparaben, with a preferred range between 0.1 wt % and 01.25 wt %; and propylparaben in the range of 0.01 wt % and 0.4 wt %, most preferably between 0.3 wt % and 0.4 wt %.

Specific benzoic acids having between twelve and fifteen carbon atoms and alkyl esters can be added to an embodiment for the formula. For example, flowers of Benzoin; flowers of Benjamin; Phenylformic Acid, and Benzoic Acid, C7H6O2, can be used. Benzoic Acid is the simplest acid of the aromatic series. Although the acid is of minor significance as a medicinal agent, it derivatives and salts constitute an important group of valuable medical agents. The addition of this component to the formula, enable the formulation to act as an antifungal agent chiefly in combination with salicylic acid as well as being an anesthetic. When the Emu oil contains enough benzoic acid it can then be used in the treatment of athletes' feet and to a lesser extent in the management of ringworm, for humans and animals. Benzoin is preferably used in amounts between 10–33 wt % and most preferably 10 wt %.

Allantoin can also be used. Specifically, Allantoin-5-Ureidohydantoin, C4H6N4O3, can be added to the formula. Allantoin is used topically as a vulnerary to stimulate tissue repair in suppurating wounds, resistant ulcers, acne seborrhea, and basic dermatological infections. It is also included in some topical preparations for oral and dental use. It is frequently combined with antiseptics and antifungal drugs. The silver salt is used in the topical treatment of extensive burns. Typically, from about 0.2 wt % to about 2.0 wt % of this ingredient can be used, particularly when the formulation is used as creams, lotions or shampoo.

The formulation uniquely can be sterilized. Traditionally, sterilization has broken down the components of oils, which contain these types of fatty acids. The objective of a sterilization process is to remove or destroy all microorganisms in or on a preparation and to assure in this way the preparation is free of infectious hazards when used with a patient. Since the variety and amounts of the variety and amounts of sterile materials required for health care have increased in significant proportions, sterilization technology has become increasingly important. Alternatively, if sterilization of the oil is not preferred, then a disinfectant can be added to the formula to render the skin noninfectious. A usable disinfectant may be an antiseptic or a germicide.

The present formulation also contemplates a spray on transdermal formula having the additional transdermal effect of promoting the transdermal delivery of additional antiseptic, antifungal, and pain relieving medicine by proliferating new skin cell growth and development.

Healing of a skin wound in mammals is a mixture of regeneration, replacement, or substitution of a new cell type for an old one. Scarring is the result of replacement. If more cells are regenerated, less scarring will result after the wound is healed.

Wound healing typically follows a fairly typical time course in mammals. The presence of pathogens can lengthen the recovery time (Hackam and Ford, 2003). Generally, within a few minutes of the initial damage to the tissue a plug of platelets and other blood products, also known as blood clots, form at the site of tissue damage and stops further loss of blood.

Within hours of receiving the wound, debris-eating white blood cells called neutrophils invade the area of damage, signaling the start of the inflammation response. Inflammation is a series of events that includes increased blood flow, increased blood vessel permeability, activation of pain receptors, and intense consumption of cell debris and bacteria by neutrophils and other white blood cells. Neutrophils ingest introduced bacteria and dead and dying cells in the wound. Neutrophils are themselves killed in the process. The accumulating mixture of dead neutrophils and fluid forms pus. Typically within a few days, the surface of the clot has dried to form a scab. Now macrophages, which are another type of specialized white blood cell, infiltrate the wound and ingest dead neutrophils and other cellular debris.

Within a week after the wound occurred, tough, fibrous cells called fibroblasts move in from surrounding connective tissue and start to multiply at the wound site. The fibroblasts begin to secrete collagen fibers. At the same time, new epidermis begins to regenerate. New endothelial cells from neighboring undamaged tissue begin to form new capillaries that grow into the repairing wound site to supply blood to the newly forming epidermis.

Within a few weeks, the rapidly dividing epidermis completely lines the original wound site. The fibroblasts generate new connective tissue or scar tissues, which replaces the epidermis destroyed by the wound. Scar tissue persists after the healing of particularly severe wounds.

The speed and effectiveness of skin wound repair depends on several factors (Burns et al., 2003). Proper nutrition is essential (Russell 2001). Vitamins C, D, E, and K all play important roles at some stage in the tissue repair process (Casey, 2003). Agents that increase cell division, such as the Emu oil found in present formulation, also hasten wound healing (Snowden et al., 1997; Politis and Dmytrowich, 1998; Lopez et al., 1999).

The oleic-rich Emu oil within the present formulation enables epidermal tissue to regenerate, restore, and rebuild in the wound itself and in underlying dermal and subcutaneous tissue. The effect of the oleic-rich Emu oil fortifies the non-necrotic epidermal and dermal cells and revitalizes potential necrotic cells. (Snowden et al., 1997; Politis and Dmytrowich, 1998; Lopez et al., 1999). A major clinical benefit of the present formulation is the reduction of the wound sepsis rates due to the formulation's proven antibacterial properties.

The present formulation also provides improved rates of wound closure, including surgical incisions and reduced healing times. The formula also reduces wound debridement and increases epidermal cell proliferation, while maintaining and feeding skin cells with linoleic acid. Further, the development of proud flesh, a common ailment in wound treatment in horses, is retarded or even prevented. Reduced scarring is evident, leading to improved function such as range of motion, contour and profile of healed skin, normalization of skin pigmentation, markings and hair coat.

The applicants recently sponsored an investigation at a microbiology laboratory at the University of North Texas located in Denton, Tex. The investigation has conclusively proven that the present formulation has statistically significant, and potent, anti-bacterial properties. The composition is especially effective against *Staphylococcus aureus, Enterococcus faecalis*, and *Pseudomonas aeruginosa* which are three common pathogens in animal and mammal wounds.

A variety of *Escherichia coli* bacteria are present in nature. They are usually found in the intestines of healthy humans and healthy animals. Even though these bacteria offer beneficial properties, there are those variations, or strains, that are pathogenic or have the ability to cause disease. *Escherichia coli* 0157:H7 is one particular strain that is also an emerging cause of foodborne illness. Symptoms such as bloody diarrhea and abdominal cramps may be observed or no such symptoms may appear. The elderly and children under five years old are highly susceptible to Hemolytic Uremic Syndrome, a disease in which red blood cells are destroyed and kidneys fail (Kendrick & Wrobel-Woerner, 1997).

The *Salmonella* germ is actually a group of bacteria that can cause diarrhea illness in humans. They are microscopic living creatures that pass from the feces of people or animals, to other people or other animals. There are many different kinds of *Salmonella* bacteria. *Salmonella* serotype *Typhimurium* and *Salmonella* serotype *Enteritidis* are the most common in the United States. *Salmonella* has been known to cause illness for over 100 years. Many different kinds of illnesses can cause diarrhea, fever, or abdominal cramps. Determining that *Salmonella* is the cause of the illness depends on laboratory tests that identify *Salmonella* in the stools of an infected person. These tests are sometimes not performed unless the laboratory is instructed specifically to look for the organism. Once *Salmonella* has been identified, further testing can determine its specific type, and which antibiotics could be used to treat it.

*Pseudomonas aeruginosa*, a versatile Gram-negative bacterium, grows in soil, marshes, and coastal marine habitats, as well as on plant and animal tissues. The bacterium *Pseudomonas aeruginosa* causes significant infections in humans. People with cystic fibrosis, burn victims, individuals with cancer, and patients requiring extensive stays in intensive care units are particularly at risk.

*Staphylococcus aureus* is the most common cause of food borne illness. Commonly called staph, this bacterium produces a poisonous toxin that causes the illness. Symptoms of staphylococcal food poisoning are usually rapid and in many cases serious, depending on individual response to the toxin, the amount of contaminated food eaten, the amount of toxin in the food ingested, and the general health of the victim. The most common symptoms are nausea, vomiting, abdominal cramping, and prostration. Some individuals may not always demonstrate all the symptoms associated with the illness. In more severe cases, headache, muscle cramping, and changes in blood pressure and pulse rate may occur. Recovery generally takes two days. It is not unusual for complete recovery to take three days and sometimes longer.

The *enterococcus* previously *Streptococcus faecalis*, causes many of the same problems as other members of the intestinal flora. These include opportunistic urinary tract infections and wound infections. In contrast to the Enterobacteriaceae, enterococcal infection is often associated with bacteria, which can lead to endocarditis or colonization of previously damaged heart valves. Little is known about its pathogenesis. The D in an older name, group D strep, refers to the Lancefield classification which is based on the antigenicity of a carbohydrate which is soluble in dilute acid and called the C carbohydrate. Lancefield identified 13 types of C carbohydrate, designated A through O, which could be serologically differentiated. The organisms that most commonly infect humans are found in groups A, B, D, and G. Streptococci that do not contain the C carbohydrate substance are called viridans streptococci or non-typable streptococci.

*Bacillus cereus* has been recognized as an agent of food poisoning since 1955. Between 1972 and 1986, 52 outbreaks of food-borne disease associated with *B. cereus* were reported to the CDC, but this is thought to represent only 2% of the total cases, which have occurred in that time. *B. cereus* causes two types of food-borne intoxications as opposed to infections. One type is characterized by nausea and vomiting and abdominal cramps and has an incubation period of 1 to 6 hours. It resembles *Staphylococcus aureus* food poisoning in its symptoms and incubation period. This is the short-incubation or emetic form of the disease.

The second type is manifested primarily by abdominal cramps and diarrhea with an incubation period of 8 to 16 hours. Diarrhea may be a small volume or profuse and watery. This type is referred to as the long-incubation or diarrheal form of the disease and resembles more food poisoning caused by *Clostridium perfringens*. In either type, the illness usually lasts less than 24 hours after onset. In a few patients symptoms may last longer.

*Candida albicans* is one of the most commonly encountered human pathogens, causing a wide variety of infections ranging from mucosal infections in generally healthy persons to life-threatening systemic infections in individuals with impaired immunity. Oral and esophogeal *Candida* infections are frequently seen in AIDS patients. Few classes of drugs are effective against these fungal infections, and all of them have limitations with regard to efficacy and side effects. *Candida albicans* is also the major fungal pathogen of humans. Infections can be localized, such as vaginal infections and oral infections, which cause a considerable degree of discomfort. In some patient groups, whose defense system is severely compromised, as in prematurely born infants, leukemics and burn patients, the yeast can turn into a deadly pathogen causing systemic infections, up to 50% of the patients infected die as a result.

The incidence of such infections is increasing rapidly, especially in hospitalized patients. In New Zealand, such infections are now eight times more frequent than they were 9 years ago. The current reservoir of anti-*Candida* drugs is very limited, and these agents can have severe side effects. Development of new strategies for the prevention and treatment of candidiasis is therefore probably the most important challenge to be faced by medical mycology today. One of the prerequisites to developing such strategies is the knowledge of how *Candida albicans* causes disease. Until recently the prevailing assumption was that *Candida* infections are simply caused by strains already present on the patient as commensals.

Using computer-assisted DNA fingerprinting with the probe Ca3, the most accurate *Candida albicans* typing method currently available, a vast of evidence is present to challenge this view. It seems that commensal strains are frequently replaced by other, more aggressive strains, derived from a single group of ubiquitous, regardless of geographic region or patient type prevalence. These strains seem responsible for approximately one third to half of all *Candida* infections worldwide. Our evidence suggests that these strains may not only be more virulent but also more resistant to antifungal drugs than other strains.

*Streptococcus agalactiae* is a gram-positive obligate pathogen that affects pre-milking heifers, as well as older cows in dairy herds. It is considered one of the major causes of economic losses to dairy producers without a control program. Although *Streptococcus agalactiae* can live outside the udder for short periods of time in the right conditions, it is considered to be an obligate pathogen of the udder. A high percentage of cows may be affected in herds where control procedures are not implemented. Fomites such as strip cups, towels, milkers' hands, cross suckling calves, milking machines and other milking equipment and unsanitary conditions are all potential sources of infection in cows. Even mastitis preparations can be a potential source of infection for the udder.

*Streptococcus agalactiae* may be transmitted from udder to udder in many ways. *Streptococcus agalactiae* breaks the natural barriers of the udder, enters the teat canal, and ascends in the milk through the quarter. The bacterium penetrates the acinar epithelium, causing edema and extravasation of neutrophils into the lumen, resulting in subclinical or clinical mastitis as well as possible systemic infection. In later stages, the acini become filled with scar tissue which plugs the glandular-ductal system resulting in a chronic, smoldering infection which decreases milk production and increases the somatic cell count of the quarter. Poor udder health due to *Streptococcus agalactiae* is slowly progressive over time, causing fibrosis and atrophy of the affected quarter. An individual cow with a high somatic cell count typically has lower production that correlates with increased somatic cell count of the herd.

The following test results were conducted on the present formulation. The project that produced the results was performed D. A. Kunz, Ph.D. of the Department of Biological Sciences at the University of North Texas, Denton. The organisms tested included *Escherichia coli, Salmonella typhimurium, Pseudomonas aeruginosa, Staphylococcus aureus, Enterococcus faecalis, Bacillus cereus, Candida albicans*, and *Streptococcus agalactiae*.

The test involved growing test cultures of inocula. All bacteria were grown as shelf cultures at 37° C. with the exception of *Candida albicans* that was grown at 30° C. The medium was Mueller-Hinton (M-H), which is the standard used for antimicrobial susceptibility testing.

The test samples were added to sterile diluted liquid culture medium such that after addition the total volume was 5 ml (see below). All tubes were then inoculated with 0.1 ml of an overnight broth culture (~1–2×$10^6$ cells [CFU]) and growth determined after 24 h by reading the culture turbidity with a spectrophotometer. The MIC is defined as the lowest concentration of the Emu oil composition inhibiting growth as evidenced by a lack of detectable turbidity.

The standard dilution scheme was as follows

|  | 10 X M–H | Water | Sample |
|---|---|---|---|
| 0% Concentration | 0.5 | 4.50 | 0 |
| 5% Concentration | 0.5 | 4.25 | 0.25 |
| 2% Concentration | 0.5 | 4.40 | 0.10 |
| 1% Concentration | 0.5 | 4.45 | 0.05 |
| 0.5% Concentration | 0.5 | 2 | 2.5 of 100 |
| 0.2% Concentration | 0.5 | 3.5 | 1.0 of 100 |
| 0.1% Concentration | 0.5 | 4.0 | 0.5 of 100 |

The results of the liquid culture test was as follows:

| | | Turbidity (Growth) at a Concentration (MIC†) | | | |
|---|---|---|---|---|---|
| | | 0 | 0.5% | 1% | 5% |
| *Escherichia coli* JM101 A | 1 day | 1.351 | 1.024 | 0.516 | 0.045 | 2% |
| *Escherichia coli* JM101 B | 1 day | ND | 1.002 | 0.408 | 0.058 | 2% |
| *Enterococcus faecalis* A | 1 day | 0.961 | 0.473 | 0.209 | 0.020 | 2% |
| *Enterococcus faecalis* B | 1 day | ND | 0.478 | 0.229 | 0.046 | 2% |
| *Pseudomonas aeruginosa* A | 1 day | 0.607 | 0.648 | 0.368 | 0.024 | 2% |
| *Pseudomonas aeruginosa* B | 1 day | ND | 0.886 | 0.560 | 0.021 | 2% |
| *Salmonella typhimurium* A | 1 day | 1.199 | 0.838 | 0.453 | 0.030 | 2% |
| *Salmonella typhimurium* B | 1 day | ND | 0.749 | 0.270 | 0.016 | 2% |
| *Staphylococcus aureus* A | 1 day | 0.760 | 0.547 | 0.518 | 0.009 | 5% |
| *Staphylococcus aureus* B | 1 day | 0 | 0.582 | 0.475 | 0.004 | 5% |
| *Bacillus cereus* A | 1 day | 0.500 | 0.768 | 0.673 | 0.034 | 5% |
| *Bacillus cereus* B | 1 day | ND | 0.900 | 0.661 | 0.048 | 5% |
| *Candida albicans* A 30° C. | 1 day | 0.411 | 0.506 | 0.100 | 0.11 | 5% |
| *Candida albicans* B 30° C. | 1 day | ND | 0.624 | 0.182 | 0.06 | 5% |
| *Streptococcus agalactiae* A | 1 day | 0.467 | 0.394 | 0.316 | 0.064 | 5% |
| *Streptococcus agalactiae* B | 1 day | ND | 0.387 | 0.340 | 0.074 | 5% |

In the above table, the values represent turbidity (growth) measurements at 540 nm. The reference blanks contained sterile medium with the Emu oil composition at the concentrations shown less cells. The identification ND stands for "not determined" and the identification MIC stands for "Minimal Inhibitory Concentration".

The test was also completed with as a solid plate or spray test. Sprayed plates with the Emu oil composition were tried and compared the number of survivors in the presence and absence of agent with Staph, Pseud and Entero but no significant differences in viability were experienced.

The conclusion from the tests is that the Emu oil composition showed antimicrobial activity at relatively high concentrations.

The formulation may be embodied in many forms without departing from the spirit or essential characteristics of the formulation.

The present embodiments are therefore to be considered in all respects as illustrative and not restrictive, the scope of the formulation being indicated by the appended claims rather than by the foregoing description. All changes, which come within the meaning and range of equivalency of the claims, are therefore intended to be embraced therein.

While only a few embodiments of the formulation have been disclosed in the above detailed description, the formulation is not limited thereto but is susceptible to various changes without departing from the scope of the formulation.

What is claimed is:

1. An analgesic, anesthetic and anti-pruritic formulation comprising:
   a. from about 10.0 wt % to about 75.0 wt % Emu oil;
   b. from about 10.0 wt % to about 33.0 wt % bezoin and derivatives thereof;
   c. from about 0.5 wt % to about 4 wt % lidocaine;
   d. from about 0.01 wt % to about 13 wt % alkyl esters;
   e. from about 0.25 wt % to about 5.0 wt % allantoin;
   f. from about 0.1 wt % to about 5.0 wt % methylparaben; and wherein the formulation is adapted to inhibit microbial activity from *Escherichia coli, Salmonella typhimurium, Pseudomonas aeruginosa, Staphylococcus aureus, Enterococcus faecalis, Bacillus cereus, Candida albicans, Streptococcus agalactiae* or combinations thereof, and perform an antipruritic function.

2. The formulation of claim 1, further comprising from about 0.1 wt % to about 2.0 wt % propylparaben.

3. The formulation of claim 2, comprising about 2.0 wt % of lidocaine.

4. The formulation of claim 2, wherein the lidocaine relieves pain on the epidermis of humans and animals for skin irritations, wounds, or burns.

5. The formulation of claim 1, wherein the Emu oil is a refined and sterilized Emu oil and wherein the refined and sterilized Emu oil ranges from about 60 wt % to about 65 wt %.

6. The formulation of claim 5, wherein the refined and sterilized Emu oil comprises at least 70 wt % linoleic and linolenic acids in combination.

7. The formulation of claim 6, wherein the formulation comprises about 20 wt % linoleic and from about 1 wt % to about 2 wt % linolenic acid.

8. The formulation of claim 1, comprising about 61.5 wt % of Emu oil.

9. The formulation of claim 1, comprising from about 10 wt % to about 20 wt % of bezoin and derivatives thereof.

10. The formulation of claim 9, comprising about 20.0 wt % of bezoin and derivatives thereof.

11. The formulation of claim 1, comprising about 2.0 wt % of allantoin.

12. The formulation of claim 1, comprising about 1.25 wt % of methylparaben.

13. The formulation of claim 1, further comprising about 0.4 wt % of propylparaben.

14. The formulation of claim 1, further comprising a member selected from the group consisting of a germicide, a bacteriacide, an antiseptic, an antifungal, a bacteriastatic agent and combinations thereof.

15. The formulation of claim 1, wherein the formulation is prepared in a form selected from the group consisting of a gel, a lotion, a spray, a patch, and an enhanced oil.

16. The formulation of claim 1, comprising from about 10 wt % to about 33 wt % of benzoin.

17. An analgesic, anesthetic, and anti-pruritic spray-on transdermal formulation comprising:
   a. from about 10.0 wt % to about 75.0 wt % Emu oil;
   b. from about 10.0 wt % to about 33.0 wt % bezoin and derivatives thereof;
   c. from about 0.01 to about 1.3 wt % alkyl esters;
   d. from about 0.25 wt % to about 5.0 wt % allantoin;
   e. from about 0.1 wt % to about 5.0 wt % methylparaben;
   f. from about 0.1 wt % to about 2.0 wt % propylparaben;
   g. from about 0.5 wt % to about 4 wt % lidocaine; and
   h. sufficient and effective amounts of environmentally safe propellants, wherein the formula is adapted to inhibit microbial activity from *Escherichia coli, Salmonella typhimurium, Pseudomonas aeruginosa, Staphylococcus aureus, Enterococcus faecalis, Bacillus cereus, Candida albicans, Streptococcus agalactiae* or combinations thereof, and perform an antipruritic function.

18. The formulation of claim 17, comprising about 2.0 wt % of lidocaine.

* * * * *